(12) United States Patent
Govari et al.

(10) Patent No.: US 7,996,057 B2
(45) Date of Patent: Aug. 9, 2011

(54) ULTRASOUND CATHETER CALIBRATION WITH ENHANCED ACCURACY

(75) Inventors: Assaf Govari, Haifa (IL); Andres Claudio Altmann, Haifa (IL); Meir Bar-Tal, Zichron Ya'acov (IL); Dror Trumer, Hadera (IL)

(73) Assignee: Biosense Webster, Inc., Diamond Bar, CA (US)

( * ) Notice: Subject to any disclaimer, the term of this patent is extended or adjusted under 35 U.S.C. 154(b) by 672 days.

(21) Appl. No.: 11/969,541

(22) Filed: Jan. 4, 2008

(65) Prior Publication Data

US 2008/0183075 A1    Jul. 31, 2008

Related U.S. Application Data

(60) Provisional application No. 60/887,457, filed on Jan. 31, 2007.

(51) Int. Cl.
*A61B 5/05* (2006.01)
(52) U.S. Cl. ......... 600/407; 600/409; 600/410; 324/219
(58) Field of Classification Search .................. 600/407, 600/437, 409, 410; 382/306–309
See application file for complete search history.

(56) References Cited

U.S. PATENT DOCUMENTS

| | | | |
|---|---|---|---|
| 5,844,140 A * | 12/1998 | Seale | 73/633 |
| 6,138,495 A | 10/2000 | Paltieli et al. | |
| 6,192,735 B1 | 2/2001 | Nagai | |
| 6,266,551 B1 | 7/2001 | Osadchy et al. | |
| 6,370,411 B1 | 4/2002 | Osadchy et al. | |
| 6,517,484 B1 | 2/2003 | Wilk et al. | |
| 6,585,561 B2 | 7/2003 | Tokutake et al. | |
| 6,585,651 B2 | 7/2003 | Nolte et al. | |
| 6,690,963 B2 | 2/2004 | Ben-Haim et al. | |
| 6,716,166 B2 | 4/2004 | Govari | |
| 6,773,402 B2 | 8/2004 | Govari et al. | |
| 2003/0006759 A1* | 1/2003 | Govari | 324/207.13 |
| 2004/0254458 A1* | 12/2004 | Govari | 600/437 |
| 2006/0036170 A1 | 2/2006 | Lachaine et al. | |
| 2007/0106156 A1 | 5/2007 | Altmann et al. | |

FOREIGN PATENT DOCUMENTS

EP    1481637 A    12/2004

OTHER PUBLICATIONS

Partial European Search Report re: 08250368.1 dated May 29, 2008.

* cited by examiner

*Primary Examiner* — Tse Chen
*Assistant Examiner* — Joel F Brutus
(74) *Attorney, Agent, or Firm* — Louis J. Capezzuto

(57) ABSTRACT

An apparatus for calibration of a probe that includes a magnetic position sensor and an acoustic imaging device has a rigid mechanical framework. One or more field generators, fixed to the framework, generate a magnetic field of known spatial characteristics. An acoustic target assembly includes a phantom coupled to a motion mechanism, which is arranged to move the phantom in a known orbit relative to the framework. A jig, fixed to the framework, holds the probe within the magnetic field of the one or more field generators, in an orientation suitable for the imaging device to image the phantom. A processor processes position and image signals from the probe in order to calibrate coordinates of the imaging device relative to the position sensor.

14 Claims, 5 Drawing Sheets

ULTRASOUND CATHETER CALIBRATION WITH ENHANCED ACCURACY

CROSS-REFERENCE TO RELATED APPLICATION

This application claims the benefit of U.S. Provisional Patent Application 60/887,457, filed Jan. 31, 2007, which is incorporated herein by reference.

FIELD OF THE INVENTION

The present invention relates generally to ultrasound imaging systems, and specifically to devices and methods for calibration of ultrasound probes.

BACKGROUND OF THE INVENTION

U.S. Patent Application Publication 2004/0254458 A1, whose disclosure is incorporated herein by reference, describes apparatus and methods for calibrating a probe having a position sensor and an ultrasonic transducer. The apparatus includes a test fixture, which includes an ultrasonic target disposed therein at a known position. A computer receives a position signal generated by the position sensor while the transducer is in alignment with the ultrasonic target. The computer thus determines the orientation of the probe in a frame of reference of the test fixture and determines calibration data for the probe responsive to the orientation of the probe.

Various methods are known in the art for calibrating position sensors. For example, U.S. Pat. Nos. 6,266,551 and 6,370,411, whose disclosures are incorporated herein by reference, describe methods and apparatus for calibrating a probe comprising a magnetic position sensor. The calibration is used to measure and compensate for variations in the positions, orientations and gains of magnetic sensor coils in the probe. To calibrate the probe, a mechanical jig holds the probe in one or more predetermined positions and orientations, and radiators generate known, substantially uniform magnetic fields in the vicinity of the jig. Signals generated by the coils are analyzed and used to produce calibration data regarding the gains of the coils and deviations of the coils from orthogonality.

Other methods for calibrating ultrasound imagers with position sensors are also known in the art. For example, U.S. Pat. No. 6,138,495, whose disclosure is incorporated herein by reference, describes a method and apparatus for calibrating a position measuring component on an imaging or scanning transducer with respect to the scanning plane. Calibrations are performed by using a calibrating device including an additional position measuring component, such that during the calibration process, the relative position of these position measuring components can be calculated. Calibrations are also performed by viewing targets in the scanning plane that are at a known position with respect to the additional position measuring component.

As another example, U.S. Pat. No. 6,585,561, whose disclosure is incorporated herein by reference, describes a calibration unit for calibrating an ultrasound head. The calibration unit is configured to receive the ultrasound head in a known position and orientation with respect to a reference portion of the calibration unit. The calibration unit allows the calibration of a coordinate system of markers associated with the ultrasound device. Echoes received from the reference portion can be used to calibrate, for example, an offset between the ultrasound head and the reference portion. The calibration unit is preferably formed of a material in which the sound velocity is known, such as a suitable plastic with a hole having a diameter to receive the ultrasound device. During calibration, echoes are received from the interface of the bottom of the calibration unit and the surrounding medium, which is preferably air. The echo can be used to calculate an offset from the ultrasound device head to the interface.

SUMMARY OF THE INVENTION

The embodiments of the present invention that are disclosed hereinbelow describe improved systems and methods for calibrating an ultrasonic imaging probe with a position sensor. These embodiments are useful particularly in calibrating ultrasound catheters, which include a transducer array and position sensor and are adapted for imaging within body cavities, such as chambers of the heart. The principles of the present invention may be applied, however, to a variety of different types of probes, for both intra- and extra-corporeal use.

In one embodiment, apparatus is provided for calibration of a probe that includes a magnetic position sensor and an acoustic imaging device. The apparatus comprises a rigid mechanical framework, which serves as the frame of reference of calibration of the imaging device relative to the position sensors. One or more field generators, fixed to the framework, generate a magnetic field of known spatial characteristics. An acoustic target assembly is also fixed to the framework. This assembly comprises a phantom coupled to a motion mechanism, which moves the phantom in a known orbit relative to the framework. A jig, fixed to the framework, holds the probe within the magnetic field, in an orientation suitable for the imaging device to image the phantom. In this configuration, a processor receives position signals from the position sensor and image signals from the imaging device, and processes the signals in order to calibrate the coordinates of the imaging device relative to the position sensor.

In another embodiment, an ultrasound phantom for calibration of a probe comprises walls shaped so as to define an interior space, which is wholly or partly enclosed by the walls. The walls comprise multiple calibration targets at different, respective positions. One or more field generators generate an energy field of known spatial characteristics in a vicinity of the phantom. The probe is inserted into the interior space defined by the walls and is moved through multiple locations and orientations. While the probe is in the interior space, a processor receives position signals from the position sensor and image signals from the imaging device, and processes the position and image signals in order to calibrate coordinates of the imaging device relative to the position sensor.

The present invention will be more fully understood from the following detailed description of the embodiments thereof, taken together with the drawings in which:

DETAILED DESCRIPTION OF EMBODIMENTS

Figure 1:
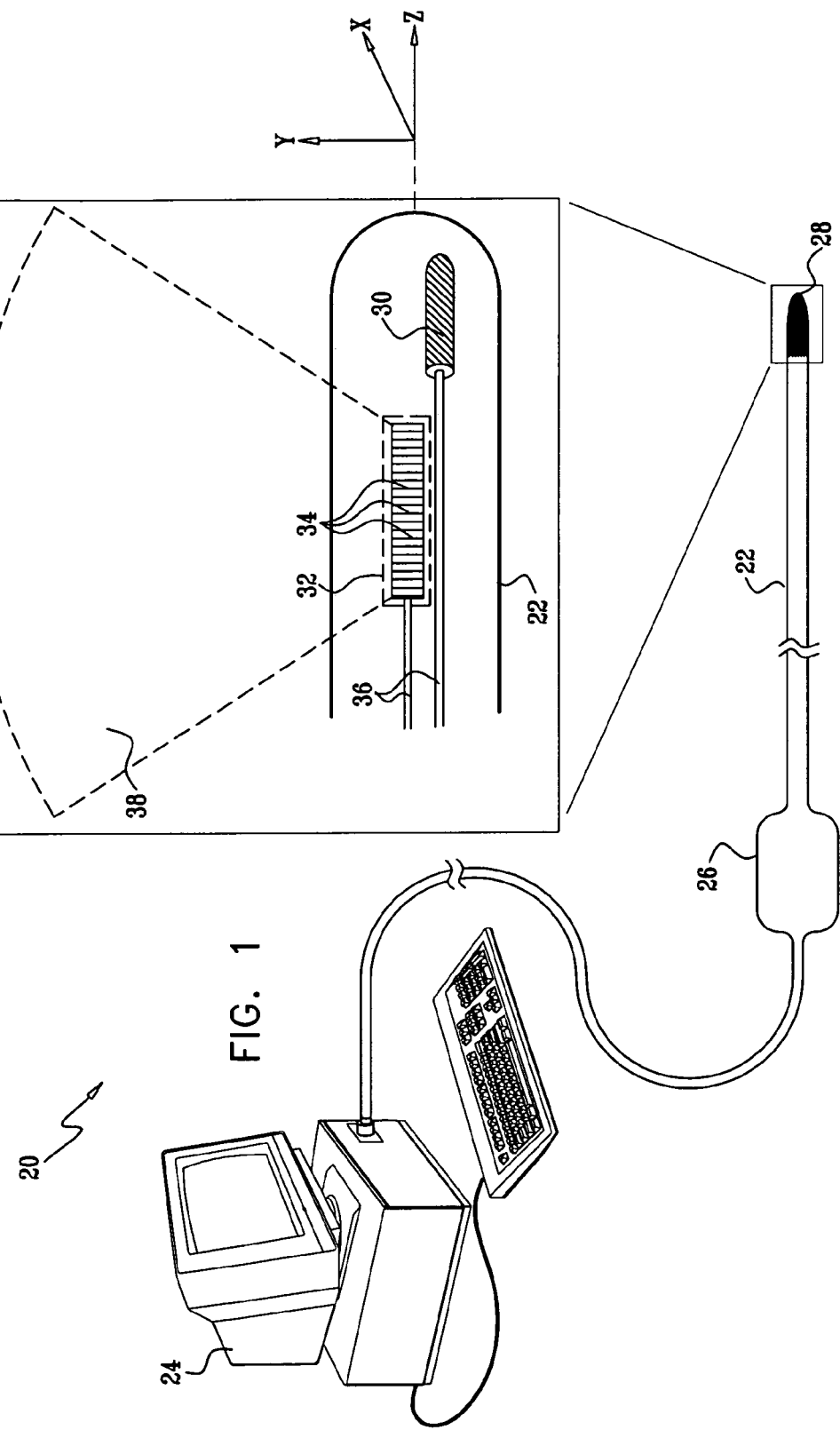
FIG. 1 is a schematic, pictorial illustration of a catheter-based system for ultrasonic imaging, in accordance with an embodiment of the present invention.

FIG. 1 is a schematic, pictorial illustration of an ultrasonic imaging system 20 comprising an elongate probe, such as a catheter 22, for insertion into the body of a patient, in accordance with an embodiment of the present invention. System 20 comprises a console 24, which typically comprises a computer processor with suitable signal processing and user interface circuits. This console receives and processes signals from catheter 22, as described hereinbelow. Typically, the console enables a user to observe and regulate the functions of catheter 20 and displays images that are formed using the catheter. Catheter 20 typically includes a handle 26 for controlling operation of the catheter by the user. The handle or a connector coupling the catheter to console 24 may comprise a microcircuit for storing calibration data, as described in the above-mentioned U.S. Pat. No. 6,266,551, for example.

A distal end 28 of catheter 22 comprises an ultrasound imaging device 32, which is used to produce ultrasound images of the inside of the body. An enlarged, cross-sectional view of distal end 28 is shown in the inset in FIG. 1. Ultrasound imaging device 32 typically comprises a phased array of transducers 34, which is operated, as is known in the art, so as to create a two-dimensional image "fan" 38 in the plane of the scanning ultrasonic beam (referred to herein as the "beam plane" or "image plane"), which contains the longitudinal axis of the catheter (identified as the Z-axis in the figures). The transducers receive ultrasonic waves that are reflected from objects in the beam plane and output signals in response to the reflected waves. Typically, these signals are processed by console 24 in order to form and display ultrasound images. Alternatively or additionally, ultrasound transducers 34 may be used for other diagnostic purposes, such as Doppler measurements, or for therapeutic uses.

Distal end 28 of catheter 22 further comprises a position sensor 30, which generates signals that indicate the position and orientation of the catheter within the body. Based on these position signals, console 24 determines the location and orientation of each fan image captured by imaging device 32. The console is thus able to determine the coordinates of objects appearing in the fan image, as well as to combine multiple images captured at different catheter positions.

Position sensor 30 is typically adjacent to imaging device 32 in a fixed locational and orientational relationship. In some embodiments, the position sensor comprises one or more coils, which produce signals in response to a magnetic field generated by a field generator outside the patient's body. The signals are analyzed by console 24 in order to determine position and orientation coordinates of distal end 28. This sort of magnetic position sensing is described in detail, for example, in the above-mentioned U.S. Pat. No. 6,266,551. Other exemplary systems that combine ultrasonic imaging with magnetic position sensing are described in U.S. Pat. Nos. 6,690,963, 6,716,166 and 6,773,402, whose disclosures are incorporated herein by reference.

Alternatively, catheter 22 may comprise any other suitable type of position sensor known in the art. For example, position sensor 30 may comprise other types of field sensing devices, such as a Hall Effect sensor. Alternatively, sensor 30 may generate magnetic fields, which are detected by sensing antennas outside the body. Further alternatively, position sensor 30 may operate by measuring impedance of the body to electrical signals or by transmitting or receiving ultrasonic position signals. The principles of the present invention are applicable to substantially any position sensing technology that can be implemented in a medical probe.

As shown in FIG. 1, due to physical constraints in the construction of catheter 22, position sensor 30 and ultrasound imaging device 32 are both located in catheter 22 at certain respective distances from the distal tip of the catheter. (This configuration of the position sensor and imaging device is shown by way of example, and the principles of the present invention may similarly be applied to other arrangements of these elements, including side-by-side arrangements.) The actual position and orientation of fan 38 is computed by taking into account the distance between the position sensor and the ultrasound imaging device. It has been found empirically that because of deviations in the process of manufacturing catheter 22, this distance typically varies from one catheter to another. Furthermore, the axes of the position sensor and of the ultrasonic transducer array in imaging device 32 may not be precisely aligned with the Z-axis or with one another other, thereby introducing additional variation in determining the orientation of fan 38.

These and other sources of alignment variation are described in greater detail in the above-mentioned Patent Application Publication US 2004/0254458 A1. If not corrected, the alignment variation will cause errors in determining the position coordinates of objects appearing in image fan 38. Certain methods for calibrating and correcting for these alignment variations are described in US 2004/0254458 A1, while other methods are described in U.S. Patent Application Publication US 2007/0106156 A1, whose disclosure is incorporated herein by reference. Other, enhanced systems and methods for calibration are described hereinbelow.

Figure 2:
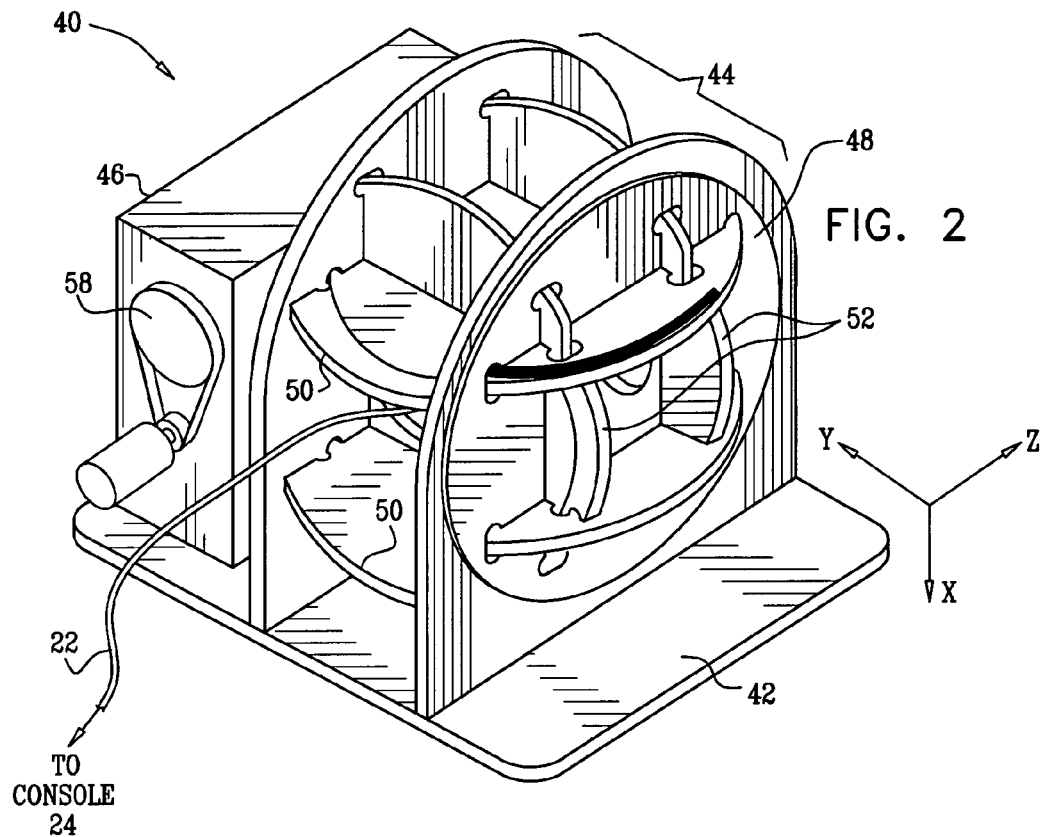
FIG. 2 is a schematic, pictorial illustration of a system for calibration of an ultrasonic imaging catheter, in accordance with an embodiment of the present invention.
Figure 3:
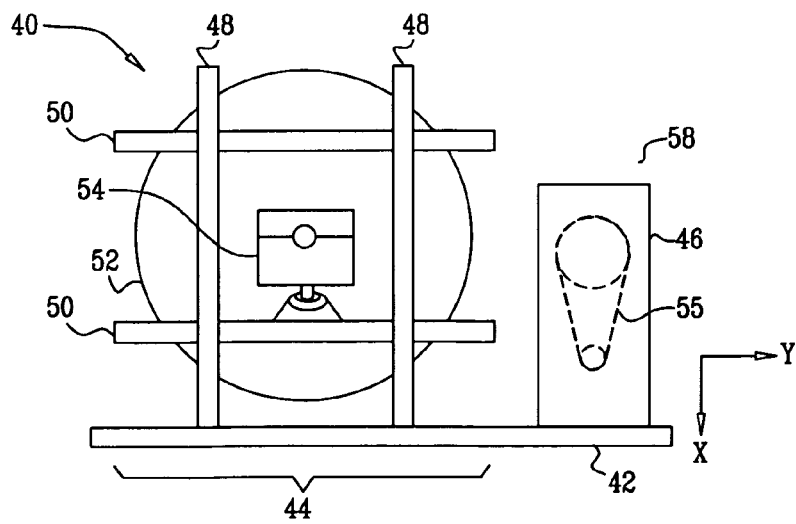
FIGS. 3 and 4 are schematic side and top views of the system of FIG. 2.
Figure 4:
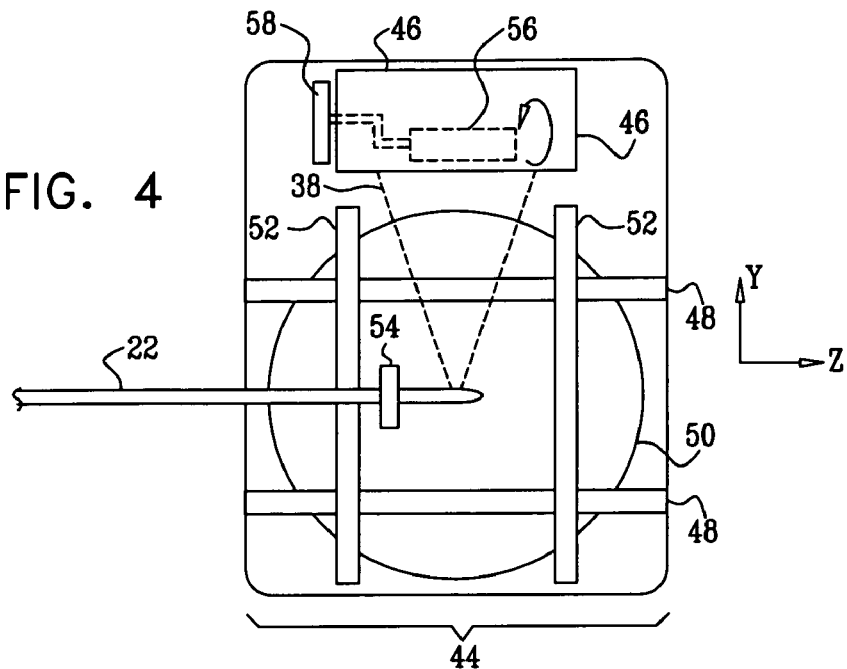

Reference is now made to FIGS. 2-4, which schematically illustrate a system 40 for calibration of an ultrasonic imaging catheter, in accordance with an embodiment of the present invention. FIG. 2 is a pictorial illustration, while FIGS. 3 and 4 are side and top views, respectively. System 40 comprises a base 42, which serves as a rigid mechanical framework for a set of magnetic field generators 44 and an acoustic target assembly 46. Various types of field generators may be used in this context. In this embodiment, the field generators comprise three pairs of Helmholtz coils 48, 50 and 52, each pair oriented along one of the X, Y and Z axes.

Figure 5:
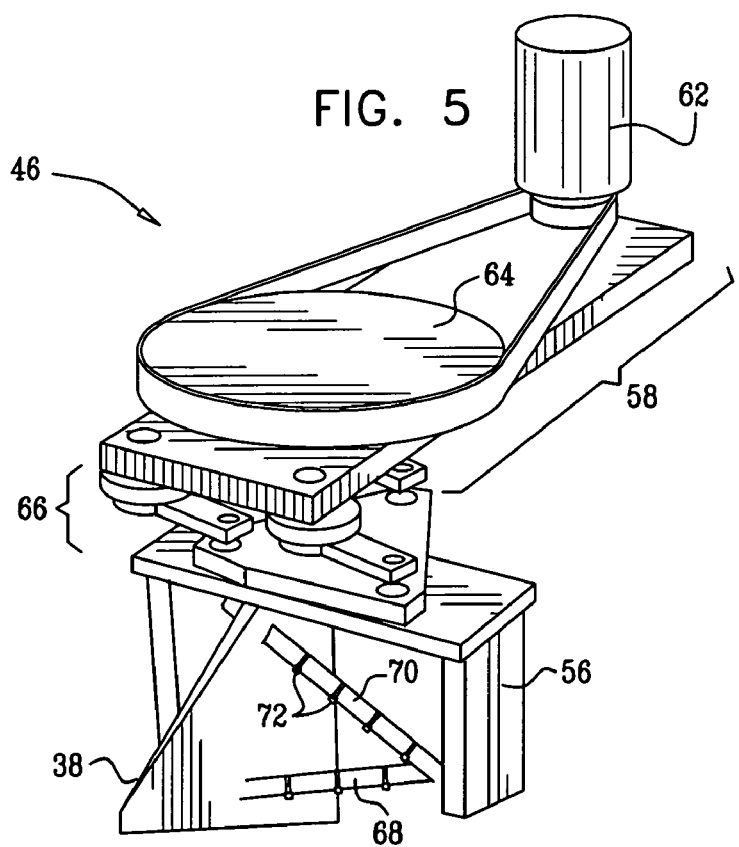
FIG. 5 is a schematic, pictorial illustration of an acoustic target assembly, in accordance with an embodiment of the present invention.
Figure 6:
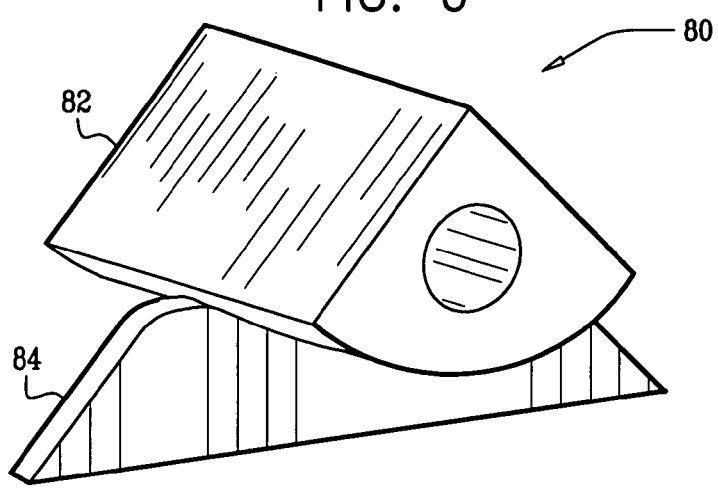
FIG. 6 is a schematic, pictorial illustration of an ultrasound phantom, in accordance with an embodiment of the present invention.

Catheter 22 is inserted into a suitable jig 54 at the center of field generators 44, with imaging device 32 facing toward target assembly 46. The target assembly comprises a phantom 56, which moves in a known orbit relative to catheter 22 within the field of view of imaging device 32, under control of a motion mechanism 58. Various types of phantoms and mechanisms may be used in the target assembly. Some particular examples are shown in FIGS. 5 and 6 and are described hereinbelow with reference thereto.

The present embodiment addresses a number of difficulties that exist in some prior ultrasound catheter calibration approaches. For example, wires, which are used in many ultrasound calibration phantoms, are smaller than the width of the ultrasound beam and therefore cause artifacts that limit their observability in the ultrasound image. In addition, inclination of the phantom relative to the ultrasound beam can cause inaccuracy in determining the precise location at which the wire crosses the beam. Other approaches use larger phantoms scanned by the ultrasound beam while measuring catheter position using an electromagnetic system. This approach relies on the accuracy of the an electromagnetic system, which is typically on the order of 1 mm.

In the present embodiment, the location readings of position sensor 30 are made in proximity to the center of a Helmholtz cell, with typical position accuracy of 0.1 mm, using gradient-calibrated electromagnetic fields generated by the three pairs of Helmholtz coils 48, 50, 52. (Optionally, the sensitivity of the sensor may first be calibrated in a uniform magnetic field.) The sensor is placed in proximity to the center of the coils. The coils in each pair are driven with currents running in opposite directions, so that the electromagnetic field in the center has nearly-constant gradient. Because the three pairs of Helmholtz coils are orthogonal to one another, the three electromagnetic fields have gradients in the three orthogonal directions.

Before calibrating catheter 22, the Helmholtz electromagnetic fields are calibrated using a mechanically-accurate sensor at known points in the volume that will be used for calibrating the catheter position sensor. The measured positions are referred to a predefined mechanical origin, which is fixed in the frame of reference of base 42. From these measurements, the Helmholtz electromagnetic field is accurately mapped as a function of location. When catheter sensor 30 is then placed in the calibrated volume, the position and orientation of the sensor may be calculated to an accuracy of 0.1 mm, which is typically much better than the operational accuracy of the electromagnetic tracker system used in actual operation of catheter 22. This high accuracy is due to the high gradient present in the Helmholtz chamber.

FIG. 5 is a schematic, pictorial illustration showing details of acoustic target assembly 46, in accordance with an embodiment of the present invention. In this embodiment, motion mechanism 58 comprises a motor, which drives a rotor 64 to move phantom 56 in a fixed orbit via a linkage 66. Phantom 56 comprises lines 68 and 70 that cross the image plane of fan 38. Lines 68 and 70 are non-parallel to improve the estimation calculation of the image coordinate system. In addition to the set of lines, point sources 72 may be placed in several locations on the phantom. These point sources, for example, may take the form of protrusions on the lines in the phantom, as shown in the figure. These latter elements improve the accuracy of the calibration, especially for parameters that are most affected by the low resolution of the ultrasound image in the direction perpendicular to the ultrasound beam plane.

During calibration, phantom 56 is moved in an accurate orbit in front of imaging device 32, typically in a circular orbit having an axis roughly parallel to the axis of the array of transducers 34. Motion mechanism 58 is built, as shown in FIG. 5, so that each of lines 68 and 70 in the target cuts the ultrasound beam at a low inclination during the entire orbit. (In other words, each line always remains parallel to its original orientation.) Many images are captured in this manner at different positions of the phantom in the orbit. Optionally, a position sensor (not shown) may be fixed to phantom 56, so as to enable electromagnetic registration of the phantom in each image, relative to the fixture base. The positions of the lines intersecting the ultrasound beam plane are extracted from the images. The intersection points from all the images in the ultrasound coordinate system are transformed to the corresponding coordinates in the fixed frame of reference of base 42.

The image origin in the fixed coordinate frame is defined by solving the following minimization expression:

$$\underset{\{az, e1, r1, x0, y0, z0\}}{\mathrm{argMin}} \left( \sum_i \left\| \vec{P}_i - \vec{P}_i(az, e1, r1, x0, y0, z0) \right\|^2 \right)$$

Here $\vec{P}_i$ is the {col,row} measurement of the intersection point of each of the lines (arranged in a predefined order), and $\vec{P}_i(az, el, rl, x0, y0, z0)$ is an analytical function of the line intersection with the ultrasound plane as a function of the plane origin (x0,y0,z0) and orientation coordinates (az, el, rl). The minimization problem can be solved using any suitable numerical or analytical method known in the art.

Using the methods described above, both the image origin of imaging device 32 and the electromagnetic origin of position sensor 30 may be determined in six dimensions (location and orientation) with high accuracy, in the same, fixed frame of reference. The relative coordinates of the origins are used to compute the calibration transformation between the electromagnetic sensor coordinates and the ultrasound image coordinates.

The techniques described herein, including the use of mechanically-accurate motion of a line phantom and building the lines from large planes that are almost invariant over the width of the ultrasound beam, improve the accuracy with which the point of intersection between the ultrasound beam and the phantom can be determined. Furthermore, integrating the electromagnetic calibration with the ultrasound phantom in a unified system provides a robust basis for calibration, whose accuracy is dependent only on the mechanical accuracy of the calibration system. This mechanical accuracy is generally better than the accuracy of both the electromagnetic position tracking and the ultrasound image measurement. The use of Helmholtz coil pairs to calibrate the electromagnetic sensor also improves accuracy, since the large electromagnetic gradient inside the Helmholtz assembly provides better estimation of the electromagnetic sensor position and orientation in comparison with most other electromagnetic tracker constructions (using single or multiple field generators).

Lines 68 and 70 in phantom 56 may be laid out in two planes that form an arrowhead pointing toward the ULS sensor (i.e., the planes meet along a line that is perpendicular to the ultrasound fan plane). As a result, the beam always reflects back diffusely from the lines, giving a clear arrowhead shape in the ultrasound image. The arrowhead shape is detected in the image, and the arrowhead location is calculated from the intersection of the two lines forming it.

FIG. 6 is a schematic, pictorial illustration of an ultrasound phantom 80, which may be used in place of lines 68 and 70, for example, in accordance with another embodiment of the present invention. Phantom 80 comprises an elongated piece 82 of triangular profile, which is shaped so as to define two spatial planes, which meet in a line, defining a sort of arrowhead shape. The phantom is typically positioned in target assembly 46 so that the line intersects the image plane of fan 38, with the arrowhead pointing toward imaging device 32. Phantom 80 further comprises a cross-piece 84, with front edges that are linear extensions of the planar surfaces of triangular piece 82. Cross-piece 84 thus defines an alignment plane, which is perpendicular to the two spatial planes of piece 82.

Figure 7A:
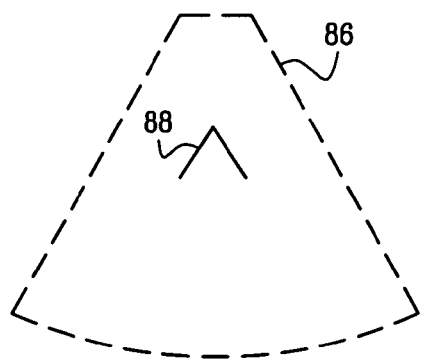
FIGS. 7A and 7B are schematic representations of ultrasound images of the phantom of FIG. 6, captured using a probe in different, respective alignments, in accordance with an embodiment of the present invention.
Figure 7B:
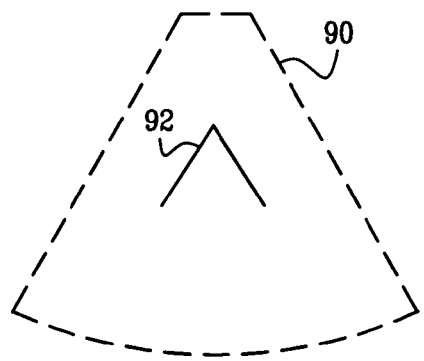

FIGS. 7A and 7B are schematic representations of ultrasound images 86 and 90 of phantom 80, captured using imaging device 32 in different, respective alignments of catheter 22, in accordance with an embodiment of the present invention. These images show how catheter 22 may be brought into precise alignment with phantom 80, such that fan 38 is parallel to and congruent with the plane of cross-piece 84 (and thus perpendicular to the planar surfaces of piece 82). In image 86, reflection of the ultrasound beam from the planes of piece 82 gives an arrowhead shape 88 having a given length. In this image, however, fan 38 is not aligned with cross-piece 84, and the cross-piece is therefore not seen in the image. In image 90, however, the image plane is aligned with the alignment plane defined by cross-piece 84. As a result, the image contains an arrowhead shape 92 of increased length relative to shape 88, due to the reflection of the acoustic waves from the linear extensions of the planes of piece 82 that are provided by cross-piece 84. Thus, the operator of system 40 is able to determine that the catheter is properly aligned in the system.

Additionally or alternatively, alignment of the catheter may be based on a virtual three-dimensional rigid body that is created by the motion of the phantom. This approach enables registration to be carried out automatically, with improved accuracy due to the triangular profiles that overcome the blurring due to the width of fan 38.

The shapes and configurations of the phantoms and target assembly in the above figures are shown only by way of example, and a wide variety of alternative shapes and configurations may be used within the scope of the present invention. Possible variations include the following:

The shape, size and orientation of the phantom may be varied.

Curves, such as harmonic curves, may be used in place of the lines in the phantom. (Examples include sine curves, circular shapes, and curves of other types.)

Different algorithms may be used for shape extraction from the ultrasound image.

Instead of extracting intersection points from each image, the ultrasound image may be analyzed by matching the image against a model of the response of the phantom to the ultrasound pulse.

The mechanical orbit that the phantom performs need not be circular, but may rather have any shape that permits enough information to be generated in order to make the computations accurately.

The phantom may be held stationary while the jig holding the catheter moves. As a result, from the point of view of the calibration procedure, the phantom can still be seen as describing a known orbit relative to the probe.

Figure 8:
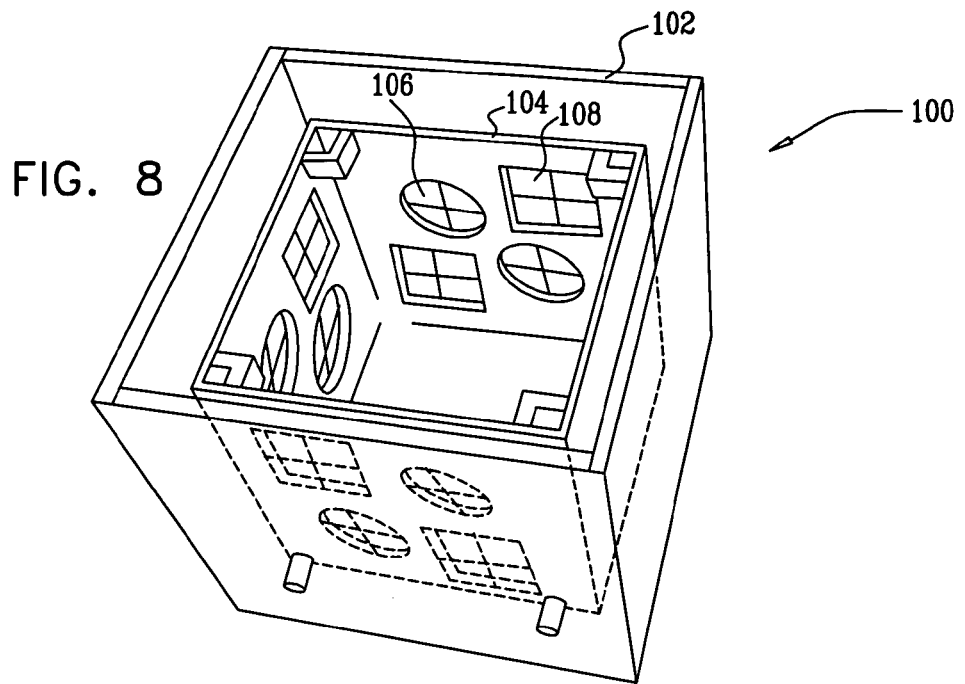
FIG. 8 is a schematic, pictorial illustration of an ultrasound phantom inside a calibration tank, in accordance with an embodiment of the present invention.
Figure 9:
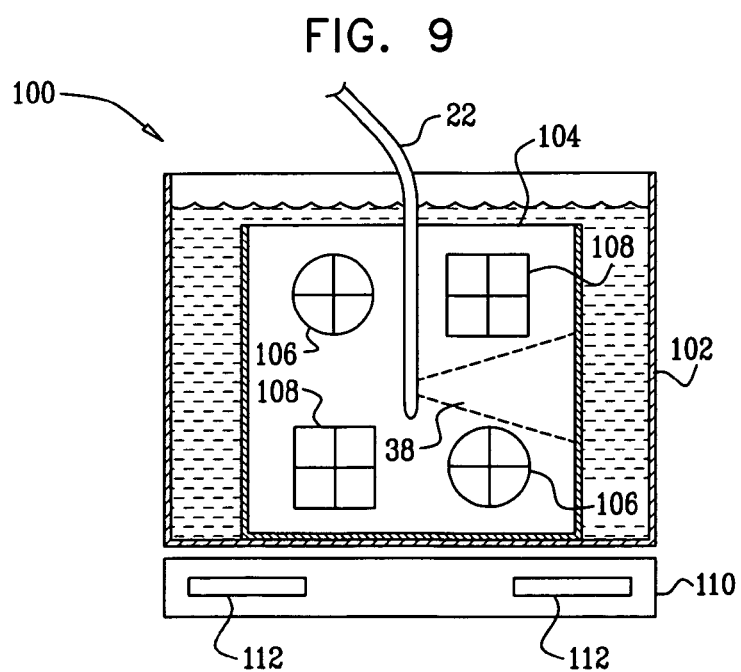
FIG. 9 is a schematic side view of a system for calibration of an ultrasonic imaging catheter, in accordance with an embodiment of the present invention.

Reference is now made to FIGS. 8 and 9, which schematically illustrate elements of a system 100 for calibration of ultrasound imaging catheter 22, in accordance with another embodiment of the present invention. FIG. 8 is a pictorial illustration showing an ultrasound phantom 104 inside a tank 102, while FIG. 9 is a side view. During calibration, tank 102 is typically filled with a suitable fluid, such as water, both inside and outside phantom 104, but the fluid is omitted from the interior of the phantom in FIG. 8 so that the details of the phantom can be seen clearly in the figure.

Phantom 104 comprises walls shaped so as to define a container, in this case a box. The walls of the box comprise multiple calibration targets 106, 108 at different, predetermined locations. Typically, as shown in the figure, the targets are located in different walls and thus are oriented in different planes. The interior space of the container has a shape and size sufficient to permit catheter 22 to be inserted into the container and moved through multiple locations and orientations, so as to aim imaging device 32 at different targets in different locations and orientations of the catheter. A location pad 110 with one or more field generators 112, such as electromagnetic coils, is placed adjacent to tank 102, and the coils are driven to generate an electromagnetic energy field of known spatial characteristics in the vicinity of phantom 104. The arrangement of field generators shown in this figure will not typically generate the sort of gradient-calibrated field that is described above, but substantially any suitable field geometry may be used in the present embodiment.

While the probe is in the interior space of phantom 104, processor 24 receives position signals from position sensor 30 in response to the electromagnetic field, and image signals from imaging device 32 due to reflection of acoustic waves from the phantom. The operator of system 100 freezes each image, marks the location of the target that appears in the image, and identifies which one of the targets it is. For each image, the magnetic position sensing system determines location and orientation coordinates of the catheter tip. The annotated images and the corresponding coordinates are used by processor 24 (or by a separate calibration processor) to calibrate the linear and angular offset of the ultrasound transducer array in the catheter relative to the position sensor. Processor 24 processes the position and image signals in order to calibrate coordinates of imaging device 32 relative to position sensor 30.

The detailed calibration procedure may be carried out as follows:

1. Calibrate the offset of the tip of catheter 22 relative to position sensor 30 in a dedicated jig (as described in the above-mentioned US 2004/0254458, for example).
2. Insert the catheter into a tube and rotate it while acquiring position coordinates in order to estimate the offset of the position sensor from the catheter axis.
3. Insert the catheter into the calibration bath and connect it to processor 24, so that the processor receives both position coordinates and ultrasound image signals.
4. Acquire data points by capturing images of different targets, as explained above. Each data point corresponds to one of the images and includes the location of the target in the image (as marked by the operator or determined automatically by the processor), the actual, known spatial coordinates of the target, and the position coordinates of the catheter, as measured using the position sensor when the image was captured.
5. Calculate a calibration transformation matrix using the set of data points. The estimation error of the matrix may be computed in order to confirm that the calibration is valid.

The use of a three-dimensional, multi-target phantom, such as phantom 104, permits fast, convenient calibration without requiring that the catheter be constrained in a jig (except in step 1, above). Although FIGS. 8 and 9 show a certain particular phantom configuration, any suitable three-dimensional arrangement of targets may be used in like manner. For example, the walls of the phantom may be arranged to define containers of different shapes, or the walls may only partially enclose the interior space that they define.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for calibration of a probe that includes a magnetic position sensor and an acoustic imaging device, the apparatus comprising:
   a rigid mechanical framework;
   one or more field generators, fixed to the framework, and operative to generate a magnetic field of known spatial characteristics;
   an acoustic target assembly, which is in a known spatial relation to the framework and comprises a phantom coupled to a motion mechanism, which is arranged to move the phantom in a known orbit relative to the framework;
   a jig, fixed to the framework, for holding the probe within the magnetic field of the one or more field generators, in an orientation suitable for the acoustic imaging device to image the phantom; and
   a processor, which is coupled to receive, while the probe is in the jig, position signals from the magnetic position sensor responsively to the magnetic field and image signals from the acoustic imaging device responsively to reflection of acoustic waves from the phantom, and to process the position and image signals in order to calibrate coordinates of the acoustic imaging device relative to the magnetic position sensor, wherein the acoustic imaging device is configured to capture two-dimensional images having an image plane, and wherein the phantom is shaped and positioned so as to define two spatial planes, which meet in a line that intersects the image plane when the probe is held in the jig in the suitable orientation.

2. The apparatus according to claim 1, wherein the phantom comprises two planar surfaces that respectively define the two spatial planes and are arranged so that the reflection of acoustic waves from the surfaces generates an arrowhead shape having a given length in the images captured by the imaging device, and wherein the phantom further comprises linear extensions of the planar surfaces that define an alignment plane, perpendicular to the two spatial planes, so that when the image plane is aligned with the alignment plane, the length of the arrowhead shape increases due to the reflection of acoustic waves from the linear extensions.

3. The apparatus according to claim 1, wherein the acoustic imaging device is configured to capture two-dimensional images having an image plane, and wherein the phantom comprises at least two non-parallel lines that cross the image plane when the probe is held in the jig in the suitable orientation.

4. The apparatus according to claim 3, wherein the phantom comprises one or more point sources on the lines.

5. The apparatus according to claim 1, wherein the acoustic target assembly is fixed to the framework.

6. The apparatus according to claim 1, and comprising a further position sensor fixed to the acoustic target assembly, wherein the further position sensor generates further position signals responsively to the magnetic field wherein the processor is operative to process the further position signals to determine the spatial relation between the acoustic target assembly and the framework.

7. The apparatus according to claim 1, wherein the one or more field generators comprise three pairs of Helmholtz coils, wherein each pair is orthogonal to the other pairs, and wherein the coils are driven to generate gradient-calibrated electromagnetic fields.

8. A method for calibration of a probe that includes a magnetic position sensor and an acoustic imaging device, the method comprising:
   operating one or more field generators, fixed to a rigid mechanical framework, so as to generate a magnetic field of known spatial characteristics;
   providing a phantom in an acoustic target assembly in a known spatial relation to the framework;
   holding the probe in a jig within the magnetic field of the one or more field generators, in an orientation suitable for the acoustic imaging device to image the phantom;
   moving at least one of the phantom and the jig so that the phantom describes a known orbit relative to the probe;
   receiving, while the probe is in the jig, position signals from the magnetic position sensor responsively to the magnetic field and image signals from the acoustic imaging device responsively to reflection of acoustic waves from the phantom; and
   processing the position and image signals in order to calibrate coordinates of the acoustic imaging device relative to the magnetic position sensor, wherein the imaging device is configured to capture two-dimensional images having an image plane, and wherein the phantom is shaped and positioned so as to define two spatial planes, which meet in a line that intersects the image plane when the probe is held in the jig in the suitable orientation.

9. The method according to claim 8, wherein the phantom comprises two planar surfaces that respectively define the two spatial planes and are arranged so that the reflection of the acoustic waves from the surfaces generates an arrowhead shape having a given length in the images captured by the acoustic imaging device, and
   wherein the phantom further comprises linear extensions of the planar surfaces that define an alignment plane, perpendicular to the two spatial planes, so that when the image plane is aligned with the alignment plane, the length of the arrowhead shape increases due to the reflection of the acoustic waves from the linear extensions.

10. The method according to claim 8, wherein the acoustic imaging device is configured to capture two-dimensional images having an image plane, and wherein the phantom comprises at least two non-parallel lines that cross the image plane when the probe is held in the jig in the suitable orientation.

11. The method according to claim 10, wherein the phantom comprises one or more point sources on the lines.

12. The method according to claim 8, wherein the acoustic target assembly is fixed to the framework.

13. The method according to claim 8, wherein a further position sensor is fixed to the acoustic target assembly and generates further position signals responsively to the magnetic field, wherein processing the position and image signals comprises processing the further position signals to determine the spatial relation between the acoustic target assembly and the framework.

14. The method according to claim 8, wherein the one or more field generators comprise three pairs of Helmholtz coils, wherein each pair is orthogonal to the other pairs, and wherein operating the one or more field generators comprises driving the coils to generate gradient-calibrated electromagnetic fields.

* * * * *